United States Patent [19]
Minoura et al.

[11] Patent Number: 4,999,297
[45] Date of Patent: Mar. 12, 1991

[54] CULTURE OF CELLS

[75] Inventors: Norihiko Minoura; Seiichi Aiba; Yukihiko Fujiwara, all of Ibaraki, Japan

[73] Assignee: Director-General of Agency of Industrial Science and Technology, Japan

[21] Appl. No.: 868,538

[22] Filed: May 30, 1986

[51] Int. Cl.$^5$ ............... C12N 5/00; C12N 11/08
[52] U.S. Cl. ............... 435/240.23; 435/180; 435/240.24; 435/240.243
[58] Field of Search ............... 435/240.23, 240.24, 435/240.241, 240.242, 240.243, 180, 289, 285, 286

[56] References Cited

PUBLICATIONS

Ishida et al, "Adhesion and growth of fibroblast on poly($\alpha$-amino acid)s containing ionic groups" Kobunshi Ronbunshu, V.42, 725-30, 1985, CA 104 (20):174584z.

Minoura et al, "Interaction between poly($\alpha$-amino acid) membranes and cells" Nippon Kagaku Kaishi (6), 1252-1258, 1985.

Kuroyanagi et al, "Preparation of copoly ($\gamma$-benzyl-L-glutamyl-$N^5$-$\beta$-D-glucopyranosyl-L-glutamine) and its interaction with fibroblast cells", Int. J. Biol. Macromol., vol. 6, 266-272, 1984.

Primary Examiner—Elizabeth C. Weimar
Assistant Examiner—Gail Poulos
Attorney, Agent, or Firm—Lorusso & Loud

[57] ABSTRACT

Cells such as mammalian cells are cultivated on a bed of a solid material whose surface is formed of a specific polymer or copolymer of an amino acid, i.e. a poly(methionine) or a copolymer of $\gamma$-benzyl glutamate.

1 Claim, No Drawings

CULTURE OF CELLS

This invention relates to a method of culturing cells for multiplication thereof in the presence of a solid surface and to a bed for culturing cells having such a solid surface.

Animal cells are generally not multiplicable in a floating or suspended state. Multiplication of animal cells occurs only when they deposit on a solid surface. Thus, in order to cultivate cells for multiplication thereof, it is necessary to use a solid surface, i. e. a bed, to which the cells are capable of depositing in a large amount.

As such a cell culturing bed, polymeric materials such as polystyrenes and polymethylmethacrylates have been hitherto used. The known culturing beds formed of such polymeric materials, however, fail to permit efficient cultivation of cells thereon because the cells cannot deposit thereon in a large amount.

It is, therefore, an object of the present invention to provide a method of culturing cells for multiplication thereof in the presence of a solid surface which permits the cells to effectively deposit thereon in a large amount. Another object of the present invention is to provide a bed for culturing cells having a solid surface which permits the effective deposition of the cells thereon.

The present inventors have made an intensive study with a view to developing new materials on which cells can deposit easily and found that specific polymers or copolymers of amino acids, i.e. poly(methionine) and γ-benzyl glutamate copolymers which provide an angle of contact with water of 60° to 70°, allow cells to deposit in a large amount and are suitable for use in culturing the cells. The present invention is based on this finding.

In accordance with the present invention there is provided a method of culturing cells for multiplication in the presence of a solid surface, characterized in that the solid surface is formed of a poly(amino acid) selected from a poly(methionine) and a γ-benzyl glutamate copolymer whose contact angle for water is in the range of 60° to 70°.

The term "bed for culturing cells" used in the present specification is intended to refer to a material having a solid surface on which the cells deposit and grow. The bed may have any suitable form such as a sheet, membrane, fiber, bead, plate or hollow thread or fiber. The term "contact angle for water" used in the present specification is intended to refer to an angle of contact between the solid surface and water measured at 25° C. by means of a goniometer type contact angle measuring device. This term is also simply referred as "contact angle" in the present specification.

The poly(amino acid) used in the present invention is a poly(methionine) or a γ-benzyl glutamate copolymer which forms a solid surface providing a contact angle for water of 60° to 70°. The γ-benzyl glutamate copolymer is a copolymer of γ-benzyl glutamate and a monomer copolymerizable with the glutamate. Illustrative of suitable copolymerizable monomers are alanine, glycine, methionine, valine, γ-methyl glutamate, γ-ethyl glutamate, β-methyl aspartate, β-benzyl aspartate, Nε-benzyloxycarbonyl lysine and Nδ-benzyloxycarbonyl ornithine. The content of the γ-benzyl glutamate in the copolymer is generally 10–90 mole %, preferably 40–80 mole %. Especially preferred copolymer is a copolymer containing 65–75 mole % of γ-benzyl glutamate and 25–35 mole % of γ-methyl glutamate.

A γ-benzyl glutamate copolymer whose contact angle is outside of the 60° to 70° range can be used for the purpose of the present invention by modifying same so as to provide a contact angle in the range of 60° to 70°. For example, a γ-benzyl glutamate-leucine copolymer which shows a contact angle of about 90° may be used for the present invention by modifying it with an aminoalcohol.

The poly(amino acid) used in the present invention may have any molecular weight as long as it can form a solid surface such as a film. Generally, however, the molecular weight of the poly(amino acid) is in the range of 10,000 to 1,000,000 daltons, preferably 20,000 to 100,000 daltons. The amino acid components constituting the copolymer may be L-amino acids, D-amino acids or racemates.

The bed for culturing cells may be prepared either by shaping the poly(amino acid) into a desired shape or by coating a surface of a substrate such as a shaped body made of a polymeric material with the poly(amino acid). Since the poly(amino acid) is generally expensive, the latter method is preferred. The polymeric substrate to be coated with the poly(amino acid) may be formed, for example, of a polyethylene, polypropylene, polystyrene, polyacrylonitrile, polymethacrylate, ethylene-propylene copolymer, polyvinyl chloride, polyester or polyamide. Both foamed and non-foamed polymeric substrate may be used. The substrate may be an inorganic one such as glass beads, glass frakes or mica.

The modification of the γ-benzyl glutamate-leucine copolymer with an aminoalcohol may be performed by contacting the copolymer with the aminoalcohol at a temperature of 20° to 90° C., preferably 50° to 80° C. The aminoalcohol may be an aliphatic or aromatic aminoalcohol having 2–12 carbon atoms. Examples of such aminoalcohols include ethanolamine, propanolamine, hydroxybenzylamine, amino-substituted polyethylene glycol having the formula $H_2N(C_2H_4O)_nH$ (where n is an integer of 2–6). The bed formed of the aminoalcohol-modified γ-benzyl glutamate-leucine copolymer may be prepared either by treating a shaped body of a γ-benzyl glutamate copolymer with an aminoalcohol or by first coating a substrate with a γ-benzyl glutamate-leucine copolymer and then treating the surface of the coated substrate with an aminoalcohol. The aminoalcohol upon contact with the copolmer reacts with a portion of the copolymer to form an amide linkage having a high hydrophilicity. The hydrophilicity of the copolymer is also improved due to the introduction of hydroxyl groups derived from the aminoalcohol. The reaction should be continued until the modified product shows a contact angle of the specified range of 60° to 70°.

The cultivation of cells may be conducted in a manner known per e except that the above poly(amino acid) is used as a solid surface on which the cells grow. Thus, the cells to be cultured are mixed with a suitable liquid or gelatinous culture medium and the mixture is allowed to stand at a temperature of, preferably, 30° to 40° C. until the cells grow, while maintaining the mixture in contact with the solid surface formed of the poly(amino acid), for example, by placing the mixture on the plate whose surface is formed of the poly(amino acid). During the cultivation, the cells deposit on the solid surface and grow at a high rate.

The present invention will explained below by way of examples. The poly(amino acid) samples used in the following examples are as shown in Table 1. The amino acid copolymers used in the examples are random copolymers.

TABLE 1

| Sample No. | Polymer | Abbreviation | Side Chain |
|---|---|---|---|
| 1 | Poly(γ-methyl L-glutamate) | PMLG | —(CH$_2$)$_2$COOCH$_3$ |
| 2 | Poly(γ-benzyl L-glutamate) | PBLG | —(CH$_2$)$_2$COOCH$_2$-Ph |
| 3 | Poly(γ-methyl L-glutamate, γ-benzyl L-glutamate) (50:50) | P(MLG-BLG) (I) | —(CH$_2$)$_2$COOCH$_3$<br>—(CH$_2$)$_2$COOCH$_2$-Ph |
| 4 | Poly(N$^\epsilon$-benzyloxycarbonyl-L-lysine, γ-benzyl L-glutamate) (70:30) | P(CLL-BLG) | —(CH$_2$)$_4$NHCOOCH$_2$-Ph<br>—(CH$_2$)$_2$COOCH$_2$-Ph |
| 5 | Poly(L-leucine, γ-benzyl L-glutamate) (70:30) | P(LL-BLG) | —CH$_2$CH(CH$_3$)$_2$<br>—(CH$_2$)$_2$COOCH$_2$-Ph |
| 6 | P(LL-BLG) modified with 3-amino-1-propanol | P(LL-BLG)-APrOH | —CH$_2$CH(CH$_3$)$_2$<br>—(CH$_2$)$_2$CONH(CH$_2$)$_3$OH<br>—(CH$_2$)$_2$COOCH$_2$-Ph |
| 7 | Poly(γ-methyl L-glutamate, γ-benzyl L-glutamate) (29:71) | P(MLG-BLG) (II) | —(CH$_2$)$_2$COOCH$_3$<br>—(CH$_2$)$_2$COOCH$_2$-Ph |

EXAMPLE 1

Films formed on the various amino acid polymers indicated in Table 1 and each having a size of 9 mm × 9 mm and a thickness of 0.05 mm were used as beds for culturing human epithelial cells. Thus, a culture liquid (0.3 ml) containing about 10$^5$/ml cells was placed on each film and allowed to stand quiescently in a room maintained at a temperature of 37° C., a CO$_2$ concentration of 5% and a humidity of 100%. The cultivation of the cells was terminated after 17 hours by rinsing the film with a phosphate buffer. Then, the number of the cells on each film was measured by a nucleal staining method. The above procedure was repeated in the same manner as described using a commercially available cell cultivation plastic film (manufactured by Wako Junyaku K.K.) as a control. The rate of deposition of cells was calculated by dividing the number of cells grown on the sample film by that grown on the control. The results are shown in Table 2 together with the contact angle of each film. In Table 2, the result obtained with the use of a polymethylmethacrylate (PMA) film is also shown for comparison purpose.

TABLE 2

| Sample Number | Polymer | Deposition Rate | Contact Angle (°) |
|---|---|---|---|
| 1* | PMLG | 39 | 54 |
| 2* | PBLG | 37 | 65 |
| 3 | P (MLG-BLG) (I) | 79 | 68 |
| 4 | P (CLL-BLG) | 70 | 66 |
| 5* | P (LL-BLG) | 14 | 88 |
| 6 | P (LL-BLG)-APrOH | 86 | 65 |
| 7 | P (MLG-BLG) (II) | 98 | 60 |

TABLE 2-continued

| Sample Number | Polymer | Deposition Rate | Contact Angle (°) |
|---|---|---|---|
| 8* | PMA | 55 | 65 |

*Comparative

EXAMPLE 2

A 1,1,2,2-tetrachloroethane solution containing poly(L-methionine) was applied on a glass plate, followed by drying in air to form a film having a thickness of about 0.05 mm. The film was then subjected to Soxhlet extraction with ethanol and dried. Using the resulting film, a cell cultivation test was conducted in the same manner as in Example 1. The cell deposition rate was found to be 71%.

EXAMPLE 3

Glass beads with a diameter of about 0.5 mm were immersed in a 0.5% solution of poly(L-methionine) in 1,1,2,2-tetrachloroethane. The solvent was then removed by evaporation to leave a culture bed composed of glass beads whose surfaces were covered with poly(L-methionine). The bed was found to show a cell deposition rate similar to that of Example 2.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method for culturing animal cells for multiplication comprising culturing animal cells on a cell adherent polymethionine surface in a culture medium.

* * * * *